United States Patent [19]

Gavish

[11] Patent Number: 5,076,281

[45] Date of Patent: Dec. 31, 1991

[54] DEVICE AND METHOD FOR EFFECTING RHYTHMIC BODY ACTIVITY

[76] Inventor: Benjamin Gavish, 65 Yasmin Street, P.O. Box 1141, Mevasseret Zion, Israel

[21] Appl. No.: 686,300

[22] Filed: Apr. 16, 1991

Related U.S. Application Data

[63] Continuation of Ser. No. 358,146, May 30, 1989, abandoned.

[30] Foreign Application Priority Data

May 31, 1988 [IL] Israel .................................. 86582

[51] Int. Cl.[5] .............................................. A61B 5/00
[52] U.S. Cl. ........................................ 128/721; 128/732; 128/905; 600/28
[58] Field of Search ................ 128/716, 721, 731-732, 128/905; 600/26-28

[56] References Cited

U.S. PATENT DOCUMENTS

| | | | |
|---|---|---|---|
| 3,991,304 | 11/1976 | Hillsman | 128/905 X |
| 4,063,550 | 12/1977 | Tiep | 128/905 X |
| 4,282,864 | 8/1981 | Pizer | 600/26 |
| 4,289,121 | 9/1981 | Kupriyanovich | 600/27 |
| 4,454,886 | 6/1984 | Lee | 128/732 |
| 4,776,323 | 10/1988 | Spector | 128/905 X |
| 4,798,538 | 1/1989 | Yagi | 128/721 X |
| 4,883,067 | 11/1989 | Knispel et al. | 600/28 |

Primary Examiner—Ruth S. Smith
Attorney, Agent, or Firm—Nixon & Vanderhye

[57] ABSTRACT

A biorhythm modulator, consisting of a sensor for monitoring biorhythmic activity of the body of a user, a circuit for continuously analyzing the biorhythmic activity and producing parameter signals based upon a biorhythmic activity, a circuit for generating selectable sound-code pattern signals, a central processing unit (CPU) connected to receive signals from both the activity characteristic parameters producing circuit and the selected sound patterns generating circuit, and to feed the signals of the parameters and patterns to a sound pattern synthesizer for producing music-like sound pattern signals, transduceable into audible music-like patterns, and having a rhythm which is non-identical to the rhythm of the biorhythmic activity. A method for modulating biorhythmic activity is also described.

11 Claims, 2 Drawing Sheets

DEVICE AND METHOD FOR EFFECTING RHYTHMIC BODY ACTIVITY

This is a continuation of application Ser. No. 07/358,146, filed May 30, 1989, now abandoned.

BACKGROUND OF THE INVENTION

1. Field of the Invention

The present invention relates to a device and method for modulating naturally occurring rhythmic body activity and more particularly to a closed-loop device and a method of utilizing musical pattern for inducing rhythms.

2. Discussion of Prior Art

Man and the higher animals respond, both psychologically and physiologically, to stimuli in the environment. Through its activating effect upon subcortical neuronal systems of the brain, sound modifies the brain's pacing of cardiovascular, endocrine, metabolic, reproductive and neurological functions.

The interaction between sound and motor activity of the body has been an acknowledged fact since the early days of human civilization. It was seen especially in the relation between dancing and music. However, the isolation of musical elements that most affect psychophysiological responses is not an easy task. It has been the subject of intensive research.

Regularly recurring sound is known to affect respiration rate and serves as a positive reinforcement of rhythmic movements, provided that respiration and movements are synchronized with the sound. An example of this is the effect of fast rhythmic drumming on the central nervous system; it affects brain wave frequencies, and leads to a state of trance.

Yet music is much more than rhythmic or non-rhythmic patterns of sound. That is why there has been much controversy about the quality and magnitude of the physical effects of music on motor responses. For example, in a variety of cultures it was believed that there exists a specific correspondence between heart rate and musical rhythm. However, scientific studies failed to confirm this hypothesis.

It has now been found that rhythmic cardiovascular activity of the body, including the pulse rate, the respiration rate and the periodic change in the diameter of small blood vessels associated with the activity of the symphathetic nervous system (the so-called "vasomotion"), as well as the brain waves respond most strongly to external stimuli with almost identical rhythm. A certain type of "resonance" phenomenon occurs when controlled musical patterns are induced in a body, causing shifts or changes in the natural body activity to a higher or lower activity or causing stabilization of the activity.

The rhythmic activities of a body are known to occur in frequency bands, which are usually non-overlapping. The electrical signal representing these activities presents instantaneous or average values. Examples of the frequency bands are as follows: Vasomotion frequency is smaller or equal to 0.1 Hz; respiration 0.15-0.4 Hz; heart beating 0.8-2 Hz; alpha, beta and theta brain wave frequencies are higher or comparable to 4 Hz. Some rhythms modulate others, e.g., respiration and vasomotion are expressed in the ECG signal by frequency modulation.

SUMMARY OF THE INVENTION

In accordance with the present invention there is therefore provided a biorhythm modulator, comprising a sensor for monitoring rhythmic activity of the body of a user, circuit means for continuously analyzing said rhythmic activity and producing activity characteristic parameter signals, means for generating selectable sound pattern signals, a central processing unit (CPU) connected to receive signals from both, said activity characteristic parameters producing circuit means and said selected sound pattern generating means and to feed the signals of said parameters and patterns to a sound pattern synthesizer for producing music-like sound pattern signals, transduceable into audible music-like patterns, and bearing selected relationship to said characteristic parameters of the rhythmic activity.

The invention further provides a method for modulating biorhythmic activity, comprising sensing the rhythmic activity of a user and transducing same into electrical signals, continuously analyzing said signals representative of the biorhythmic activity for producing activity characteristic parameter signals, generating selectable sound pattern signals, feeding said activity characteristic parameter signals and said sound pattern signals to a sound pattern synthesizer for producing music-like sound pattern signals of selected relationship to said characteristic parameter signals of the monitored biorhythmic activity, and transducing the synthesized signals into audible music-like sound to be heard by the user, thereby forming a closed-loop biorhythmic modulator.

The term "musical pattern" as used herein is meant to include not only acoustical patterns or effects, but also effects or patterns produced by optical signals similarly sensed by the body. Moreover, in conjunction with the present invention, this term may also refer to a combined effect of sound and visual patterns or effects perceivable by man or animals.

The invention will now be described in connection with certain preferred embodiments directed to a respiration modulator with reference to the following illustrative figures so that it may be more fully understood.

BRIEF DESCRIPTION OF THE DRAWINGS

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DETAILED DISCUSSION OF PREFERRED EMBODIMENTS

Figure 1A:
FIG. 1A is a perspective view of the respiration modulator attached to a user, according to the present invention.
Figure 1B:
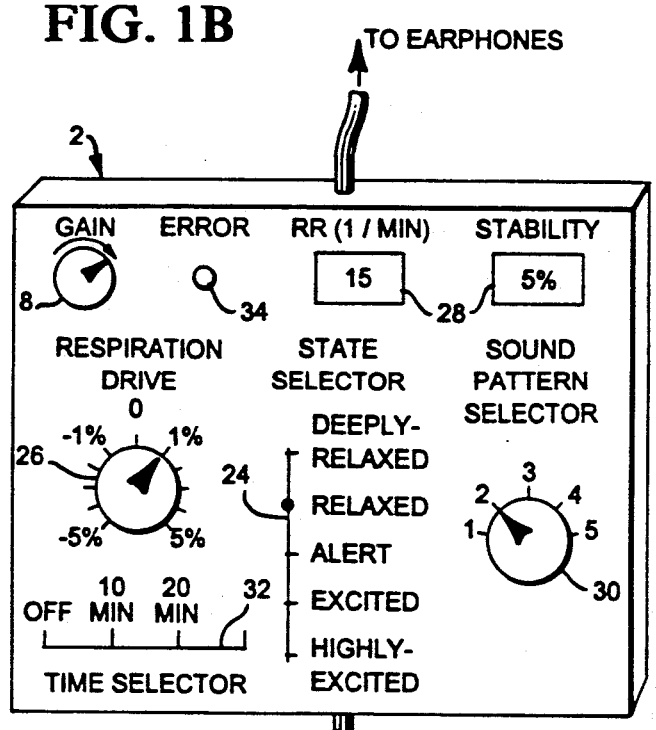
FIG. 1B is an enlarged view of the front panel of the respiration modulator of FIG. 1A illustrating selectable modulator's function adjustments.
Figure 2:
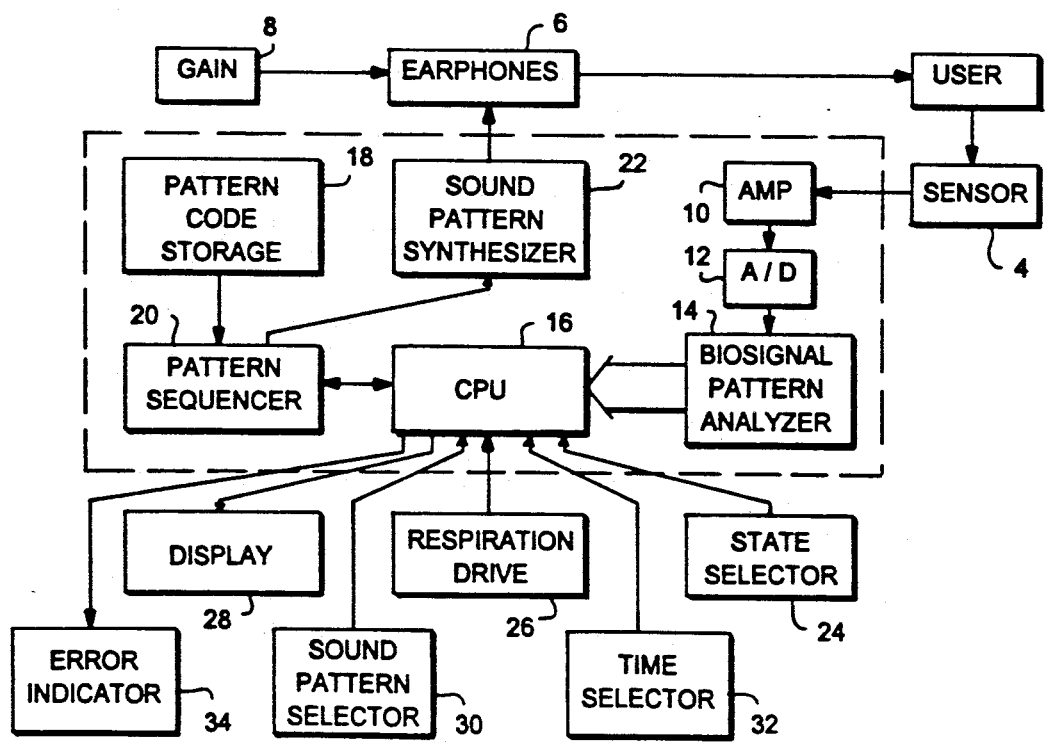
FIG. 2 is a block diagram of the biorhythm modulator of the present invention.

In the context of the particular example of a respiration modulator, there is seen in FIGS. 1A, 1B and 2 a respiration modulator 2 comprising a sensor 4, or a combination of sensors, provided that the respiration activity can be elucidated from its output. Preferably, the sensor 4 may consist of a piezoelectric transducer attached to a flexible belt affixed around a user's chest. Further seen are earphones 6 which may be replaced by a loudspeaker, the sound intensity of which is adjustable by a gain control 8. Signals from the sensor 4 are fed to a filter and amplifier 10, converted into digital signals by the A/D coverter 12, and then passed to a biosignal pattern analyzer 14 which recognizes and calculates certain parameters of the biosignal pattern and applies the parameters to the Central Processing Unit (CPU) 16. As further seen in the figures, the modulator 2 comprises pattern code storage 18 which consists of a memory containing patterns of codes which can be translated into "music" by first, transforming the patterns of code into sequences of codes signals by the pattern sequencer 20. These patterns of codes are eventually fed at a certain rhythm, phase and specificity controlled by the CPU 16, to a sound pattern synthesizer 22. The pattern sequencer 20 feeds in turn the CPU 16 with signals from which the selected sound will be generated. The synthesizer 22 converts, in real time the sound pattern codes into a "real music" which becomes audible to the user by the earphones 6 as adjusted by the gain control 8.

The operation of the CPU 16 is controlled by the user or by an operator, by means of the following controls: state selector 24, which determines the nature of the sound synthesized; respiration drive 26 which increases or decreases the rhythm of the sound synthesized patterns relative to the monitored respiration rate which can be visually displayed on the modulator, together with a respiration rate stability indication at 28; sound pattern selector 30 which selects the desired sound pattern, and the time selector 32, which sets the overall time of the system's operation and shuts it off after the termination of the set duration. In addition, as illustrated in FIG. 1B, the modulator 2 may include an error indicator 34 which emits a warning signal when the sensor 4 has not been placed properly for obtaining meaningful signals. Other parameters, such as pulse rate, if monitored, can also be displayed just as well, if desired.

The operation of the system will now be explained with reference also to FIGS. 3A and 3B.

The user (or operator) affixes the sensor around the chest, selects by the state selector 24 the nature of sound to be synthesized from the options of the states of: "Deeply relaxed", "Relaxed", "Alert", "Excited" or "Highly Excited", which are associated with the degree of biorhythmic activity. If it is desired to increase or decrease the rhythm of the sound synthesized patterns relative to the monitored respiration rate, the respiration drive 26 is turned in the clockwise or respectively, counterclockwise direction from the "0" position indicative of no change. As the biosignal pattern analyzer 14 receives in digitized form, signals as sensed by the sensor 4, it processes the same in real time, in order to calculate the following parameters from an RA curve (see FIG. 3A):

Breathing Start Times—$t(i)$, where $i = 1,2,3 \ldots$ is the breathing number;

Respiration Period—$T(i) = t(i+1) - t(i)$;

Inspiration and Expiration times—$T_{in}(i)$ and $T_{ex}(i) = T(i) - T_{in}(i)$;

Respiration Amplitude—$A(i)$;

Period Change—$dT(i+1) = T(i+1) - T(i)$;

Relative Period Change—$dT(i)/T(i)$;

Logical Variable (TRUE or FALSE)—$F(i) = 0$ if Relative Period Change is larger than, for example, 0.2, which means an interruption in breathing; otherwise $F(i) = 1$;

From these parameters other parameters are calculated in real time;

Mean Period—$T$ = Average of the last successive five $T(i)$ values for which $F(i) = 1$;

Mean Respiration Rate—$f = 60/T$ (breathings per min) provided that T is expressed in sec.;

The means of $A$, $T_{in}$, $T_{ex}$ are defined similarly;

Stability of the RR—$S = dT/T$, where $dT$ is the standard deviation of the last five $dT(i)$ values for which $F(i) = 1$.

The parameters $t(i)$, $T$, $f$, $T_{in}$, $T_{ex}$, $A$ and $S$ are applied to the CPU 16.

Taking into account the state of the respiration drive 26, the CPU 16 transforms $T$, $T_{in}$ and $T_{ex}$ into $T'$, $T'_{in}$ and $T'_{ex}$ which can be somewhat smaller or larger (but proportional values), as determined by the respiration drive 26, and feed these values to the sound pattern sequencer 20, which matches the sound pattern with the rhythm $1/T'$ and the respiration characteristics $T'_{in}$ and $T'_{ex}$. The pattern sequencer 20 sends to the CPU signals concerning the "musical period" $T'$, i.e. at times $T'$, $2T'$, $3T'$... (FIG. 3B). By comparing the phase difference between these signals and the events of breathing start time [$t(i)$ in FIG. 3A], the CPU can evaluate the capability of the sound patterns to correctly follow the breathing patterns. In case of a failure, the CPU restarts the operation of the pattern sequencer with an adjusted phase. These cases are typical to the use of the respiration drive with a difference between $T'$ and $T$, which is not too large.

Figure 3A:
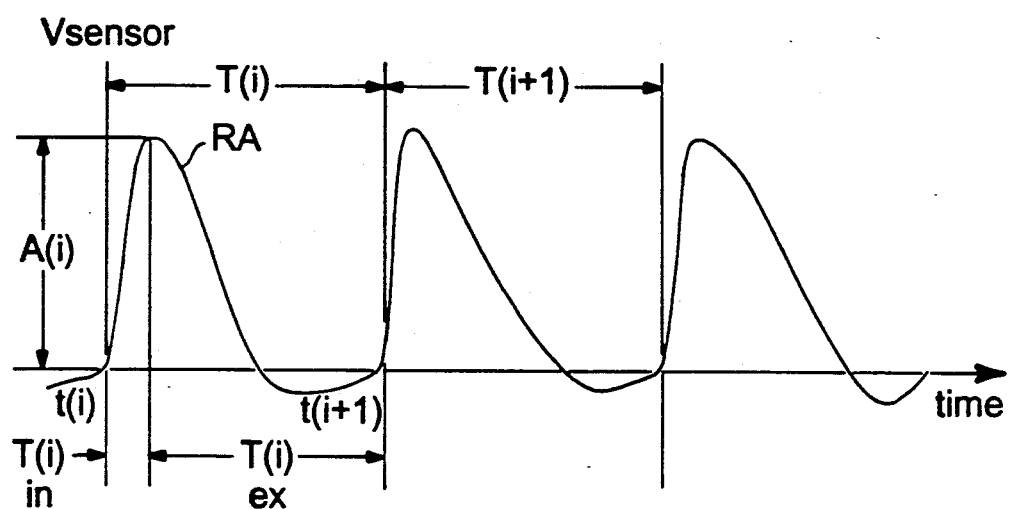
FIG. 3A is a graphic representation of a biosignal, proportional to variations in the chest circumference, and some of the parameters evaluated thereby.
Figure 3B:
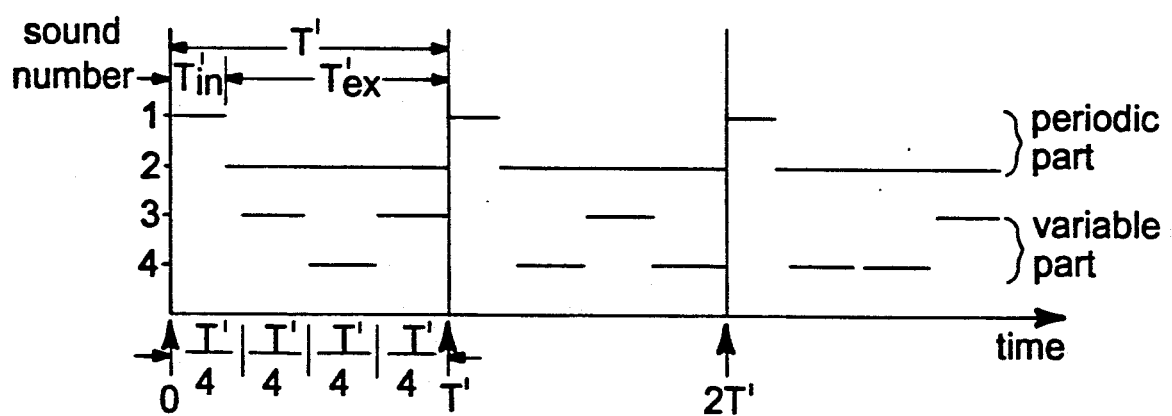
FIG. 3B is a graphic representation of an example of a synthesized sound pattern corresponding to the biosignal shown in FIG. 3A.

The synthesized sound pattern, schematically shown in FIG. 3B, contains "musical units" of a period $T'$. The generated sound resembles music played by four "instruments" identified by sound numbers 1–4. Sounds numbers 1 and 2 display a periodic pattern that resembles a breathing if number 1 is played during the inspiration time $T_{in}$, e.g., $0.2T'$ and number 2 during the expiration time $T' - T'_{in}$, e.g. $0.8T'$. In order to avoid playing a boring sound pattern, sound numbers 3 and 4 generate a background sound, which is not monotonous, every quarter of a period i.e., $T'/4$, as shown. Suppose the sound pattern played contains three "musical units", then in order to store this information it is required to specify a sequence of "events" containing a sound number, ON time and duration. Taking $T' = 1$ (a unity), the first "events" concerning sound numbers 1 to 4 are [1,0,0.2], [2,0.2,0.8], [3,0.25,0.25], [4,0.5,0.25]. In order to be meaningful to the sound pattern synthesizer, the notation sound numbers require codes for tone, intensity and a number of "musical parameters" concerning the specific musical instrument, to be simulated by the synthesizer as onset and decay times of the sound. Thus, the parameters concerning sound number together with sequences of "events" define musical pattern for a specific $T'_{in}/T'$ value i.e. fraction of time spent in inspiration, for a given $T'$. Such sequences of events are contained in the pattern code storage 18. Each sequence can be identified by a specialized code to be supplied by the CPU 16 to the pattern sequencer 20. In its simplest form, to each option of a biorhythmic activity state selection and sound pattern selection correspond a number of pattern code sequences with different $T'_{in}/T'$ values, to be matched with that of the user. Given the values of $T'$ and $T'_{in}/T'$ and the option number, the pattern sequencer identifies a sequence with $T'_{in}/T'$ value close to that supplied by the CPU and then releases the code signals to the sound pattern synthesizer 22 at "musical units" of period $T'$. However, a substantial amount of memory space can be saved by an improved pattern sequencer: for example, such a sequencer can compose a periodic pattern made of sound numbers 1 and 2 at the durations $T'_{in}$ and $T'-T'_{in}$, respectively as shown in FIG. 3B, thus making a "prerecording" of such patterns unnecessary. Furthermore, the selection of sound numbers 3 and 4 can be made randomly instead of a preselected choice.

Such musical patterns have the advantage that the same "music" can be played at any desired rhythm which is not attainable with recorded music, since slowing down or speeding up the rhythm of recorded music changes tones and nature of the sounds.

Hence, by means of predetermined selectable synthesized music which is produced by synthesizing sound pattern with real time rhythmic biosignals of a user and feeding the sound of synthesized music to be heard by the user, there is formed a closed loop system wherein a controlled variation in the rhythm and other parameters of the synthesized music can influence the respiration rate which, in turn, otherwise influences the state or degree of relaxation or excitation of the user.

It should be noted that in practice heart beats are also notable in the pattern shown in FIG. 3A and could be used to analyze pulse rate.

The sensor can monitor changes in the skin blood volume e.g., by means of an infrared photoplethysmographic transducer. Blood volume changes are translated into variations in light absorptions and then transduced into electric current signals. Such signals contain both, rhythm and amplitude of the body activity. Another example of sensors which can similarly be used are, ECG electrodes for monitoring the body's pulse rate. The body's respiration rate and neural activity appear as frequency modulations. Alternatively, there may be used EEG or EMG electrodes which monitor brain wave frequencies, and respectively, electrical activity of the muscles.

It will be evident to those skilled in the art that the invention is not limited to the details of the foregoing illustrative embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A biorhythm modulator, comprising:
   a sensor for monitoring biorhythmic activity of the body of a user;
   circuit means for continuously analyzing said biorhythmic activity and for producing parameter signals based upon said biorhythmic activity;
   means for generating selectable sound-code pattern signals;
   a central processing unit (CPU) means, responsive to signals from both said circuit means and said generating means, for supplying said parameter signals and pattern signals to a sound pattern synthesizer for producing music-like sound pattern signals, having a selectable rhythm, which signals are transduceable into audible music-like patterns and have a rhythm which is non-identical to the rhythm of the biorhythmic activity.

2. The biorhythm modulator as claimed in claim 1, wherein said sensor is a piezoelectric transducer attached to a flexible belt.

3. The biorhythm modulator as claimed in claim 1, wherein said circuit means include:
   an amplifier for amplifying the output signals of said sensor;
   an analog-to-digital converter connected at the output of said amplifier; and
   a biosignal pattern analyzer for analyzing biorhythmic activity of the user and for producing signals representative of the biorhythmic activity.

4. The biorhythm modulator as claimed in claim 3, wherein said signals representative of the biorhythmic activity are selected from the group consisting of the following measurable and calculable parameters: starting time of individual body activity periods; body activity period; times characterizing body activity changes within an activity period; body activity amplitude; change of body activity period and activity amplitude; the mean period of activity; the mean amplitude of activity; the mean rate of activity; the times characterizing activity changes within an activity period; standard deviation of period and amplitude changes; stability of period, rate and amplitude of activity; logic variables defining interruptions in biosignal in terms of predetermined changes in period and amplitude.

5. The biorhythm modulator as claimed in claim 1, wherein said means for generating selectable sound-code pattern signals include a pattern code storage means and a pattern sequencer.

6. The biorhythm modulator as claimed in claim 5, wherein said biorhythmic activity includes respiration rate, further including a respiration drive wherein said sound pattern synthesizer is connected with said pattern sequencer to receive signals representative of the code number of a specific sound-code pattern as set by said respiration drive controlling the rhythm of the selected sound-code pattern relative to said monitored respiration rate and as set by a state selector determining the nature of the selected sound-code from a defined state of lowest to highest biorhythmic activity.

7. The biorhythm modulator as claimed in claim 1 wherein said CPU means is connected with said circuit means for analyzing signals selected from the group consisting of signals representative of: the starting time of individual activity periods; the mean of activity period, rate, amplitude and times of characterizing activity changes within an activity period, and the stability of period, rate and amplitude.

8. The biorhythm modulator as claimed in claim 1, further comprising control means for controlling the operation time of the modulator.

9. The biorhythm modulator as claimed in claim 1, further comprising a display exhibiting sensed activity rate and its stability.

10. A method for modulating biorhythmic activity, comprising:

sensing the biorhythmic activity of a user and transducing same into electrical signals;

continuously analyzing said signals representative of the biorhythmic activity for producing parameter signals based upon said biorhythmic activity;

generating selectable sound-code pattern signals;

feeding said parameter signals and said sound-code pattern signals to a sound-code pattern synthesizer for producing music-like pattern signals having a rhythm which is non-identical to the rhythm of the biorhythmic activity, and transducing the music-like pattern signals into audible music-like sound to be heard by the user, thereby forming a closed-loop biorhythmic modulator.

11. The method as claimed in claim 10, further comprising the steps of selecting said music-like sound-code pattern signals from a group of pattern signals representing natures of biorhythmic states ranging from a state of lowest biorhythmic activity to a state of highest biorhythmic activity, relative to the sensed biorhythmic activity.

* * * * *